United States Patent
Mochizuki

(10) Patent No.: US 10,441,699 B2
(45) Date of Patent: Oct. 15, 2019

(54) BLOOD PURIFICATION APPARATUS

(71) Applicant: Nikkiso Company Limited, Tokyo (JP)

(72) Inventor: Hiroaki Mochizuki, Shizuoka (JP)

(73) Assignee: NIKKISO COMPANY LIMITED, Tokyo (JP)

( * ) Notice: Subject to any disclaimer, the term of this patent is extended or adjusted under 35 U.S.C. 154(b) by 39 days.

(21) Appl. No.: 15/654,880

(22) Filed: Jul. 20, 2017

(65) Prior Publication Data

US 2017/0312412 A1 Nov. 2, 2017

Related U.S. Application Data

(63) Continuation of application No. PCT/JP2016/051820, filed on Jan. 22, 2016.

(30) Foreign Application Priority Data

Jan. 23, 2015 (JP) ................. 2015-011338

(51) Int. Cl.
*B01D 19/00* (2006.01)
*A61M 1/16* (2006.01)
(Continued)

(52) U.S. Cl.
CPC ............ *A61M 1/1658* (2013.01); *A61M 1/14* (2013.01); *A61M 1/36* (2013.01); *A61M 1/3624* (2013.01);
(Continued)

(58) Field of Classification Search
CPC .... A61M 1/3676; A61M 1/16; A61M 1/3627; A61M 1/1601; A61M 1/1658;
(Continued)

(56) References Cited

U.S. PATENT DOCUMENTS

| 6,044,691 A | 4/2000 | Kenley et al. |
| 2006/0079826 A1 | 4/2006 | Beden et al. |

(Continued)

FOREIGN PATENT DOCUMENTS

| EP | 2745860 A1 | 6/2014 |
| JP | S60-153138 A | 10/1985 |

(Continued)

OTHER PUBLICATIONS

English language machine translation of JP2003093503, 16 pages, No Date.*

(Continued)

*Primary Examiner* — Pranav N Patel
(74) *Attorney, Agent, or Firm* — The Dobrusin Law Firm, PC

(57) ABSTRACT

A blood purification apparatus includes a blood circuit, a dialyzer capable of purifying the blood flowing through the blood circuit, a blood pump provided to an arterial blood circuit and that delivers the blood in the blood circuit, and an air-trap chamber capable of collecting air in the blood flowing through the blood circuit. A peristaltic pump (a substitution-fluid-infusion device) that is capable of infusing a substitution fluid is connected to the air-trap chamber. A substitution fluid layer is formable on a blood layer in the air-trap chamber. The air-trap chamber is provided with a blood-interface-detecting device that is capable of detecting an interface between the blood layer and the substitution fluid layer that are formed in the air-trap chamber. A lack of substitution fluid in the air-trap chamber is detectable on the basis of the interface between the blood layer and the substitution fluid layer that is detected by the blood-interface-detecting device.

20 Claims, 6 Drawing Sheets

(51) Int. Cl.
*A61M 1/36* (2006.01)
*A61M 1/14* (2006.01)

(52) U.S. Cl.
CPC ........ *A61M 1/3627* (2013.01); *A61M 1/3672* (2013.01); *B01D 19/0021* (2013.01); *A61M 2205/3306* (2013.01); *A61M 2205/3375* (2013.01); *A61M 2205/3389* (2013.01); *B01D 2247/08* (2013.01)

(58) Field of Classification Search
CPC ...... A61M 1/34; A61M 1/342; A61M 1/3441; A61M 1/3465; B01D 19/0021; B01D 2247/08
See application file for complete search history.

(56) References Cited

U.S. PATENT DOCUMENTS

| | | |
|---|---|---|
| 2009/0024070 A1 | 1/2009 | Gelfand et al. |
| 2009/0043240 A1 | 2/2009 | Robinson et al. |
| 2010/0168640 A1 | 7/2010 | Kopperschmidt et al. |
| 2010/0191164 A1* | 7/2010 | Sasaki ............ A61M 1/16 604/5.04 |
| 2010/0274172 A1 | 10/2010 | Guenther et al. |
| 2011/0139690 A1 | 6/2011 | Akita et al. |
| 2012/0000547 A1 | 1/2012 | Gronau et al. |
| 2013/0035626 A1 | 2/2013 | Suzuki |
| 2015/0021244 A1 | 1/2015 | Furuhashi et al. |
| 2015/0151036 A1 | 6/2015 | Furuhashi et al. |
| 2016/0250405 A1 | 5/2016 | Kogoshi et al. |

FOREIGN PATENT DOCUMENTS

| | | |
|---|---|---|
| JP | 2003-093503 | 4/2003 |
| JP | 2003-290342 | 10/2003 |
| JP | 2004-016619 A | 1/2004 |
| JP | 2005-253555 A | 4/2006 |
| JP | 2006-280775 A | 10/2006 |
| JP | 2007-007435 A | 1/2007 |
| JP | 3128724 U | 1/2007 |
| JP | 2007-167108 A | 7/2007 |
| JP | 2007-282737 A | 6/2008 |
| JP | 2009-112651 A | 5/2009 |
| JP | 2009-131412 A | 6/2009 |
| JP | 2010-000161 A | 1/2010 |
| JP | 2010-269050 A | 12/2010 |
| JP | 2010-273693 A | 12/2010 |
| JP | 2010-273784 A | 12/2010 |
| JP | 2011-161059 A | 8/2011 |
| JP | 2012-095842 | 5/2012 |
| JP | 2012-192099 A | 10/2012 |
| JP | 2013-056079 A | 3/2013 |
| JP | WO2013147075 * | 10/2013 |
| JP | 2014-097197 A | 5/2014 |
| JP | 2014-184108 | 10/2014 |
| WO | 2004/000391 | 12/2003 |
| WO | 2009004777 | 1/2009 |
| WO | 2011/099521 A1 | 5/2011 |
| WO | 2013/031965 A1 | 3/2013 |
| WO | 2015/068833 A1 | 5/2015 |

OTHER PUBLICATIONS

Extended European Search Report for Application No. 16740281.7 dated Jun. 6, 2018.
Potentially related U.S. Appl. No. 14/497,369, filed Sep. 26, 2014, published as US2015/0021244 on Jan. 22, 2015.
Potentially related U.S. Appl. No. 14/615,839, filed Feb. 6, 2015, published as US2015/0151036 on Jun. 4, 2015.
Potentially related U.S. Appl. No. 15/149,247, filed May 9, 2016, published as US2016/0250405 on Sep. 1, 2016.
Potentially related U.S. Appl. No. 15/451,653, filed Mar. 7, 2017, published as US2017/0173249 on Jun. 22, 2017.

* cited by examiner

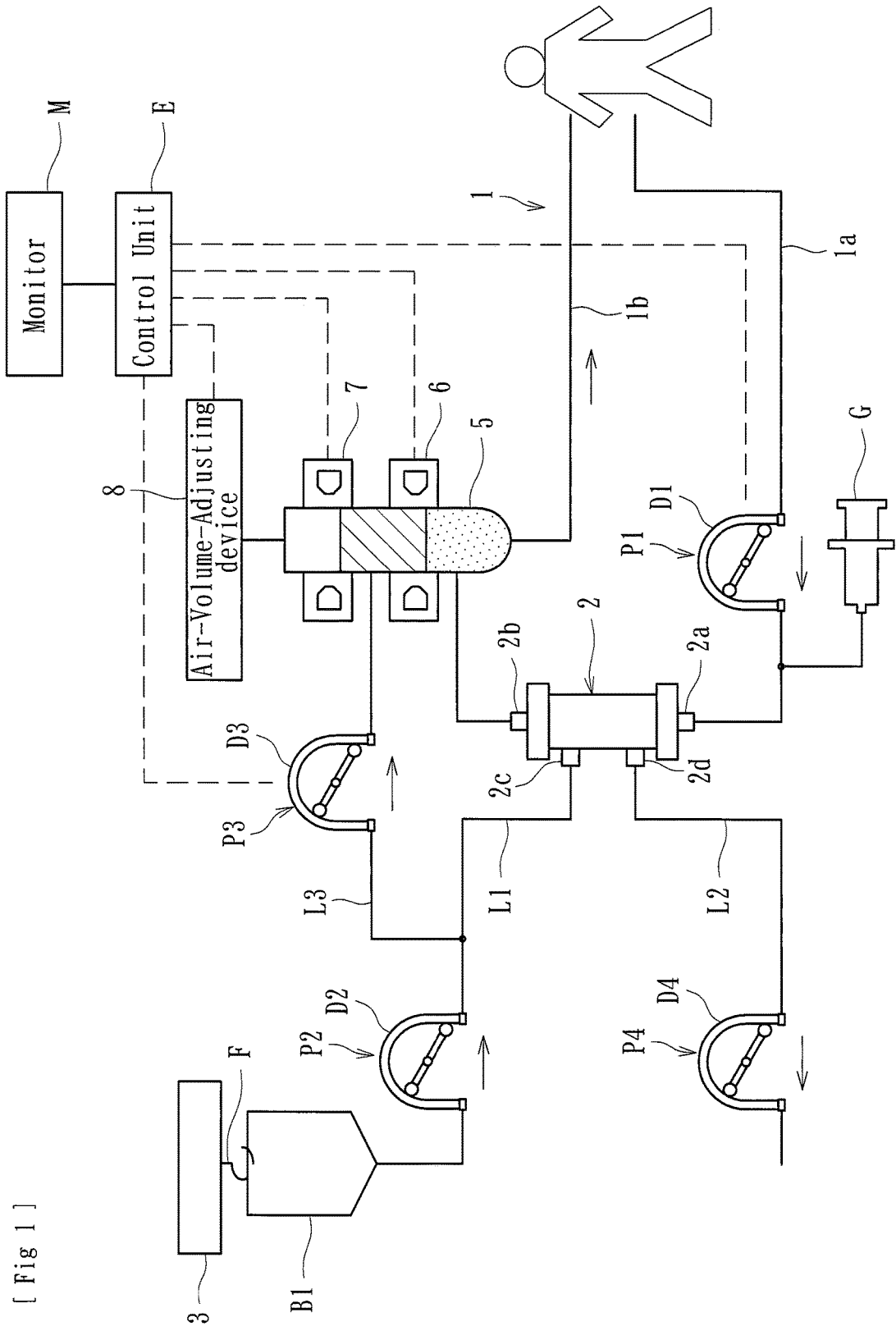
[Fig 1]

[Fig 2]
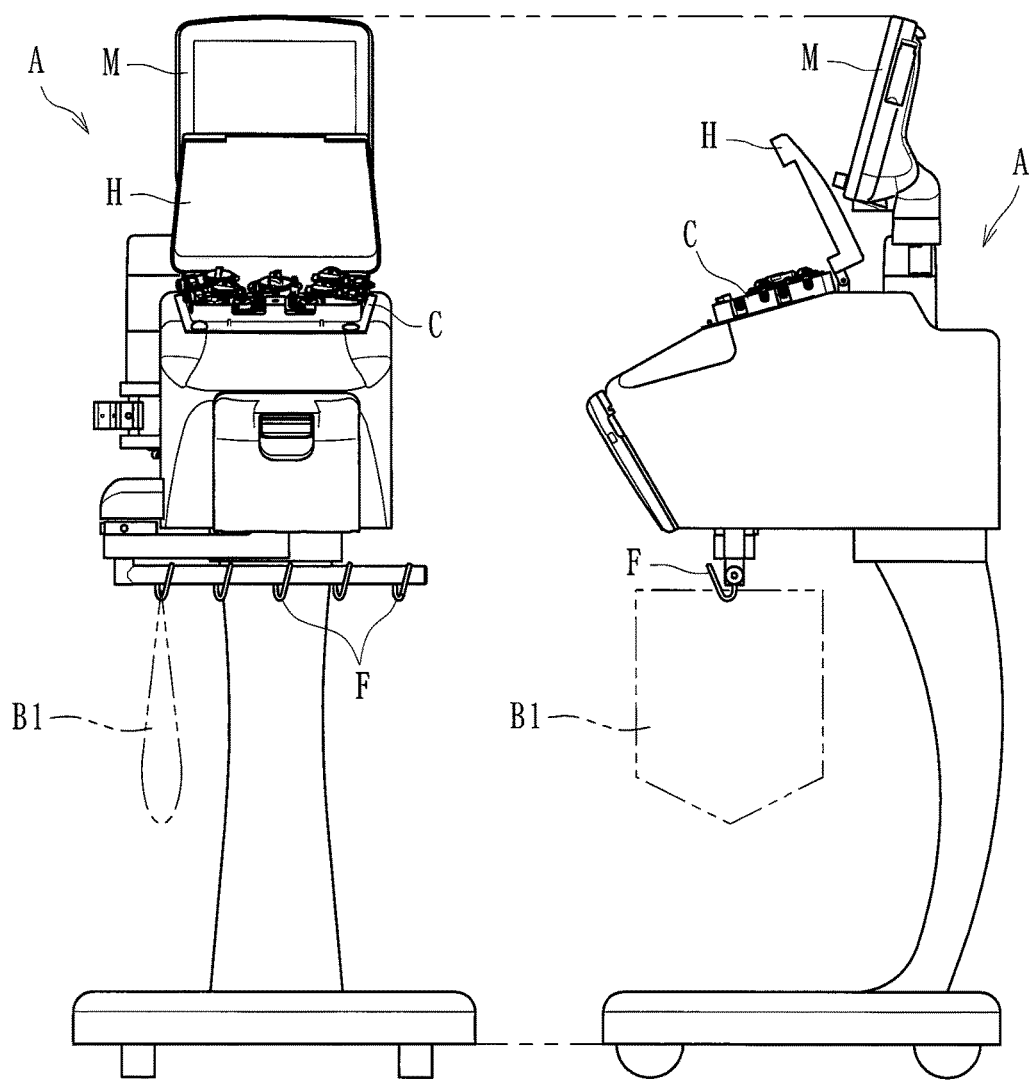

[Fig 3]
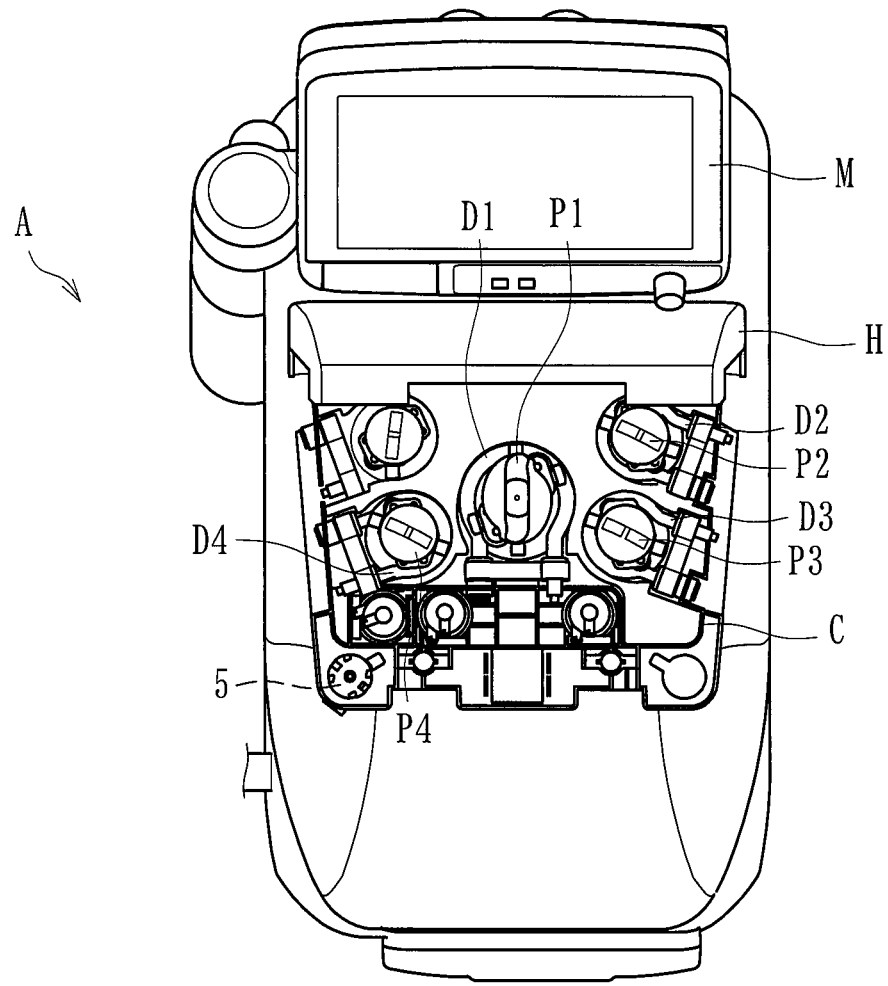

[Fig 4]
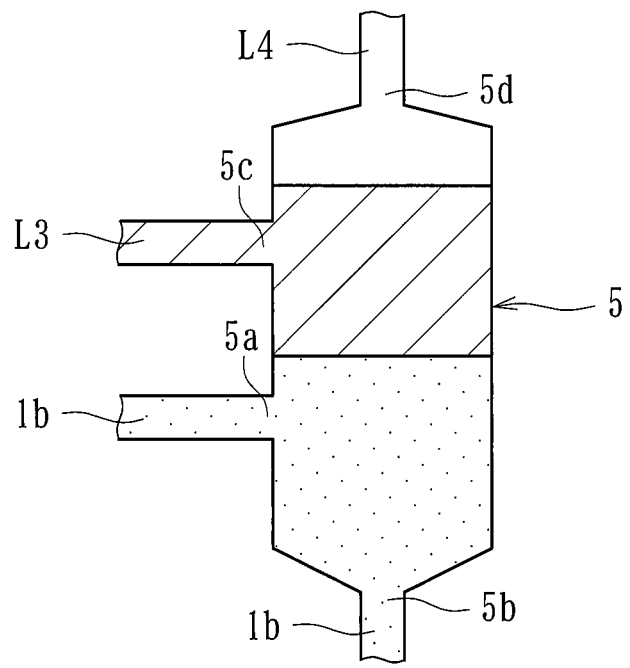
[Fig 5]
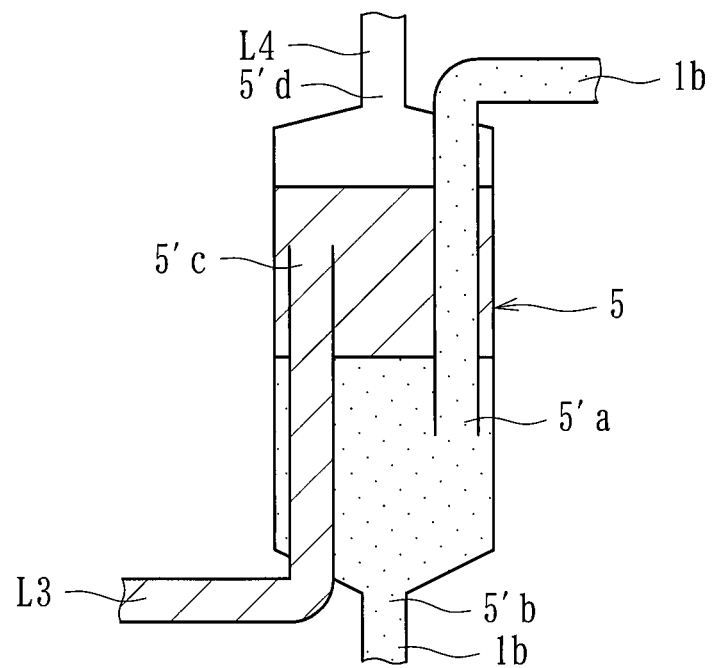

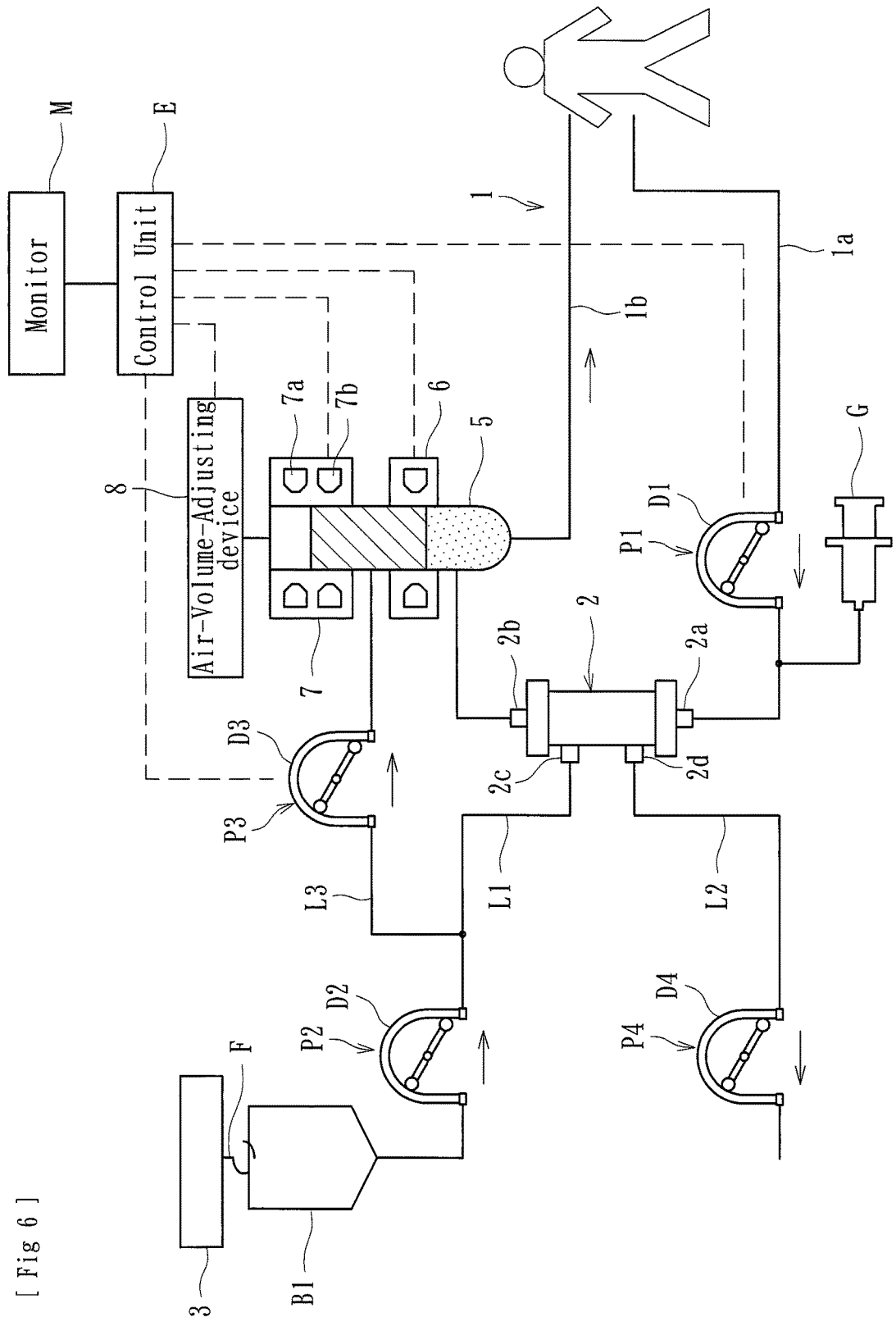
[Fig 6]

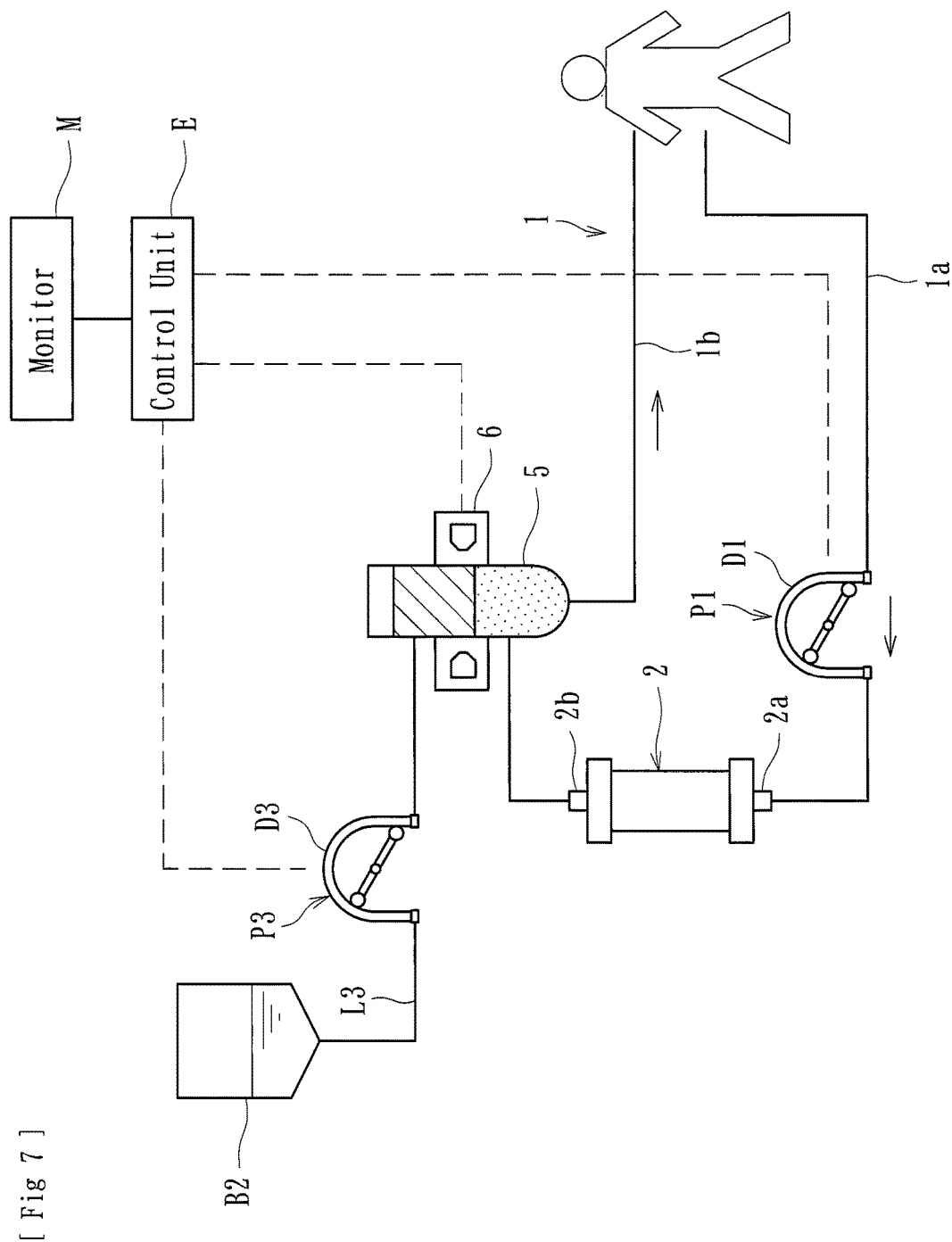

BLOOD PURIFICATION APPARATUS

FIELD

The present invention relates to a blood purification apparatus for purifying the blood of a patient while extracorporeally circulating the blood in a treatment such as a dialysis treatment performed by using a dialyzer.

BACKGROUND

In a general dialysis treatment, blood collected from the patient is extracorporeally circulated and is then returned to the body of the patient through a blood circuit. The blood circuit basically includes an arterial blood circuit and a venous blood circuit that are connectable to a dialyzer (a blood purification device) including, for example, hollow fiber membranes. The arterial blood circuit and the venous blood circuit are provided at the distal ends thereof with an arterial puncture needle and a venous puncture needle, respectively, which are stuck into the patient, whereby the blood is extracorporeally circulated during the dialysis treatment.

The arterial blood circuit, which is one of the two blood circuits, is provided with a peristaltic blood pump. When the blood pump is activated with the arterial puncture needle and the venous puncture needle being stuck in the patient, blood collected from the body of the patient can be delivered into the dialyzer while being extracorporeally circulated. Furthermore, an arterial air-trap chamber and a venous air-trap chamber are connected to the arterial blood circuit and the venous blood circuit, respectively. Bubbles contained in the blood that is under extracorporeal circulation are purged (removed) in the air-trap chambers. Then, the resulting blood is returned to the body of the patient.

Known air-trap chambers disclosed by, for example, PTL 1 and PTL 2 are each a chamber having a storing space in which an air layer, a substitution fluid layer (a layer of a physiological saline solution or the like), and a blood layer are formable in that order from the top, so that air in the blood circulating through a blood circuit is removed by being collected in the air layer. That is, the substitution fluid layer interposed between the blood layer and the air layer prevents the blood in the blood layer from directly coming into contact with the air in the air layer. Hence, the coagulation of the blood can be suppressed.

PTL 1: Japanese Registered Utility Model No. 3128724
PTL 2: Japanese Unexamined Patent Application Publication (Translation of PCT Application) No. 2005-530543

SUMMARY

The above known blood purification apparatuses have the following problem.

In the process of extracorporeally circulating the blood in the blood circuit, the substitution fluid in the substitution fluid layer formed in the air-trap chamber may gradually diffuse into the blood in the blood layer, leading to a lack of substitution fluid. Consequently, the effect of preventing the coagulation of the blood may be reduced. Nevertheless, in the known blood purification apparatus, the lack of substitution fluid is recognized by a medical worker or the like who visually checks the air-trap chamber. Therefore, the lack of substitution fluid cannot be recognized quickly and correctly, leading to a problem of a delay in taking an appropriate action against the lack of substitution fluid.

In view of the above circumstances, the present teachings provide a blood purification apparatus in which a lack of substitution fluid in an air-trap chamber can be recognized quickly and correctly.

According to the teachings herein a blood purification apparatus includes a blood circuit including an arterial blood circuit and a venous blood circuit and through which blood of a patient is allowed to extracorporeally circulate from a distal end of the arterial blood circuit to a distal end of the venous blood circuit, a blood purification device interposed between the arterial blood circuit and the venous blood circuit of the blood circuit and that is capable of purifying the blood flowing through the blood circuit, a blood pump provided to the arterial blood circuit and that delivers the blood in the blood circuit, and an air-trap chamber connected to the blood circuit and that is capable of collecting air in the blood flowing through the blood circuit. A substitution-fluid-infusion device that is capable of infusing a substitution fluid is connected to the air-trap chamber. A substitution fluid layer is formable on a blood layer in the air-trap chamber. The air-trap chamber is provided with a blood-interface-detecting device that is capable of detecting an interface between the blood layer and the substitution fluid layer that are formed in the air-trap chamber. A lack of substitution fluid in the air-trap chamber is detectable on the basis of the interface between the blood layer and the substitution fluid layer that is detected by the blood-interface-detecting device.

According to the teachings herein in the blood purification apparatus according to the present teachings, the blood purification apparatus is capable of issuing a predetermined notification if any lack of substitution fluid in the air-trap chamber is detected.

According to the teachings herein in the blood purification apparatus according to the present teachings, if any lack of substitution fluid in the air-trap chamber is detected, the blood pump or the substitution-fluid-infusion device is controlled to reduce a volume of the blood layer or to increase a volume of the substitution fluid layer.

According to the teachings herein in the blood purification apparatus according to the present teachings, the blood-interface-detecting device is capable of detecting the interface between the blood layer and the substitution fluid layer in a non-contact manner from an outer side face of the air-trap chamber and at a predetermined duty ratio.

According to the teachings herein in the blood purification apparatus according to the present teachings, an air layer is formable on the substitution fluid layer in the air-trap chamber, an air-volume-adjusting device that is capable of infusing and discharging air into and from the air layer is connected to the air-trap chamber, and the air-trap chamber is provided with an air-interface-detecting device that is capable of detecting an interface between the substitution fluid layer and the air layer that are formed in the air-trap chamber.

According to the teachings herein, the substitution-fluid-infusion device that is capable of infusing the substitution fluid is connected to the air-trap chamber, the substitution fluid layer is formable on the blood layer in the air-trap chamber, the air-trap chamber is provided with the blood-interface-detecting device that is capable of detecting the interface between the blood layer and the substitution fluid layer that are formed in the air-trap chamber, and a lack of substitution fluid in the air-trap chamber is detectable on the basis of the interface between the blood layer and the substitution fluid layer that is detected by the blood-interface-detecting device. Therefore, the lack of substitution fluid in the air-trap chamber can be recognized quickly and correctly.

According to the teachings herein, the blood purification apparatus is capable of issuing the predetermined notification if any lack of substitution fluid in the air-trap chamber is detected. Therefore, the lack of substitution fluid in the air-trap chamber can be recognized more quickly and correctly.

According to the teachings herein, if any lack of substitution fluid in the air-trap chamber is detected, the blood pump or the substitution-fluid-infusion device is controlled to reduce the volume of the blood layer or to increase the volume of the substitution fluid layer. Therefore, the lack of substitution fluid in the air-trap chamber can be solved automatically.

According to the teachings herein, the blood-interface-detecting device is capable of detecting the interface between the blood layer and the substitution fluid layer in the non-contact manner from the outer side face of the air-trap chamber and at the predetermined duty ratio. Therefore, the misdetection of the lack of substitution fluid that is caused by, for example, the pulsation generated by the driving of the blood pump can be suppressed, and the accuracy can further be increased.

According to the teachings herein, the air layer is formable on the substitution fluid layer in the air-trap chamber, the air-volume-adjusting device that is capable of infusing and discharging air into and from the air layer is connected to the air-trap chamber, and the air-trap chamber is provided with the air-interface-detecting device that is capable of detecting the interface between the substitution fluid layer and the air layer that are formed in the air-trap chamber. Therefore, the interface of the air layer in the air-trap chamber can be set to an appropriate level by using the air-volume-adjusting device. Accordingly, the substitution fluid layer can have an appropriate volume.

BRIEF DESCRIPTION OF THE DRAWINGS

FIG. 1 is a schematic diagram of a blood purification apparatus according to an embodiment of the present invention.

FIG. 2 includes a front view and a side view of a dialysis-apparatus body included in the blood purification apparatus.

FIG. 3 is a plan view of the dialysis-apparatus body.

FIG. 4 is a schematic diagram of an air-trap chamber included in the blood purification apparatus.

FIG. 5 is a schematic diagram of a modification of the air-trap chamber included in the blood purification apparatus.

FIG. 6 is a schematic diagram of a blood purification apparatus according to another embodiment of the present invention.

FIG. 7 is a schematic diagram of a blood purification apparatus according to yet another embodiment of the present invention.

DETAILED DESCRIPTION

Embodiments of the present invention will now be described specifically with reference to the drawings.

A blood purification apparatus according to an embodiment is a dialysis apparatus for giving a dialysis treatment and includes, as illustrated in FIGS. 1 to 3, a blood circuit 1, a dialyzer 2 as a blood purifier, an air-trap chamber 5, a blood-interface-detecting device 6, an air-interface-detecting device 7, an air-volume-adjusting device 8, and a dialysis-apparatus body A including elements such as a monitor M (see FIGS. 2 and 3) and a control unit E. Reference character G given in FIG. 1 denotes a syringe for infusing an anticoagulant into the blood circuit 1.

The dialyzer 2 houses, in a housing thereof, a plurality of hollow fibers each having microscopic pores. The housing has a blood-introduction port 2a, a blood-discharge port 2b, a dialysate-introduction port 2c, and a dialysate-discharge port 2d. The blood circuit 1 is made of flexible tubes and includes an arterial blood circuit 1a to the distal end of which an arterial puncture needle is attachable, and a venous blood circuit 1b to the distal end of which a venous puncture needle is attachable. The proximal end of the arterial blood circuit 1a is connected to the blood-introduction port 2a of the dialyzer 2. The proximal end of the venous blood circuit 1b is connected to the blood-discharge port 2b of the dialyzer 2.

Furthermore, a dialysate-introduction tube L1 through which dialysate is introduced into the dialyzer 2 and a dialysate-discharge tube L2 through which the dialysate (waste liquid) is discharged from the dialyzer 2 are attachable to the dialysis apparatus. The distal end of the dialysate-introduction tube L1 is connected to the dialysate-introduction port 2c of the dialyzer 2. The distal end of the dialysate-discharge tube L2 is connected to the dialysate-discharge port 2d of the dialyzer 2. The present embodiment employs a substitution-fluid-introduction tube L3 that connects the dialysate-introduction tube L1 and the venous blood circuit 1b to each other. The arterial blood circuit 1a and the venous blood circuit 1b forming the blood circuit 1, and the dialysate-introduction tube L1, the dialysate-discharge tube L2, and the substitution-fluid-introduction tube L3 are each made of a flexible tube through which liquid can flow.

Furthermore, the arterial blood circuit 1a is provided with a blood pump P1 at a halfway point thereof. The blood pump P1 is provided in a portion where a case C is attached (see FIG. 3). The blood pump P1 is a peristaltic pump including a rotor that rotates on the inner peripheral side of a stator, and a pair of rollers provided to the rotor. When the rotor rotates in the direction in which the liquid flows, the pair of rollers squeeze a squeezable flexible tube D1 connected to the arterial blood circuit 1a, whereby the liquid can be delivered.

Furthermore, as illustrated in FIG. 3, a squeezable flexible tube D2 is connected to a halfway point of the dialysate-introduction tube L1, and a squeezable flexible tube D3 is connected to a halfway point of the substitution-fluid-introduction tube L3. The squeezable flexible tube D2 and the squeezable flexible tube D3 are attached to peristaltic pumps P2 and P3, respectively, included in the dialysis apparatus. Furthermore, a squeezable flexible tube D4 is connected to a halfway point of the dialysate-discharge tube L2 and is attached to a peristaltic pump P4 included in the dialysis apparatus. When the peristaltic pump P4 is activated, the waste liquid can be discharged to the outside of the apparatus.

As with the blood pump P1, the peristaltic pumps P2 to P4 are provided in the portion where the case C is attached (see FIG. 3). The peristaltic pumps P2 to P4 each include a rotor that rotates on the inner peripheral side of a stator, and a pair of rollers provided to the rotor. When the rotor rotates in the direction in which the liquid flows, the pair of rollers squeeze the squeezable flexible tube (D2, D3, or D4) connected to the flow route, whereby the liquid can be delivered. Details of the peristaltic pumps P2 to P4 are the same as those of the blood pump P1. Hence, detailed description of the peristaltic pumps P2 to P4 is omitted.

As described above, the dialysis apparatus includes the blood pump P1 and the peristaltic pumps (P2 to P4), and the case C is provided with the squeezable flexible tubes (D1 to D4) to which the respective flow routes are connected. When the case C is attached to the dialysis apparatus, the squeezable flexible tube D1 is set to the blood pump P1 while the squeezable flexible tubes (D2 to D4) are set to the peristaltic pumps P2 to P4, respectively.

Hence, when the case C is fitted to the portion (the stators) of the dialysis apparatus where the blood pump P1 and the peristaltic pumps P2 to P4 are provided (see FIGS. 2 and 3) and a cover H is then closed, the squeezable flexible tubes (D1 to D4) can be attached to the blood pump P1 and the peristaltic pumps (P2 to P4) at a time. Then, the arterial puncture needle and the venous puncture needle are stuck into the patient, and the blood pump P1 (a blood pump) is activated. Thus, the blood of the patient can be extracorporeally circulated through the arterial blood circuit 1a and the venous blood circuit 1b.

On the other hand, a storage bag B1 that stores the dialysate to be supplied to the dialyzer 2 is connected to the proximal end of the dialysate-introduction tube L1. The dialysate-introduction tube L1 is provided at halfway points thereof with other elements such as a warming bag (not illustrated) for warming the dialysate. When the peristaltic pump P2 is activated, the dialysate in the storage bag B1 flows toward the dialyzer 2 while the dialysate (the waste liquid) in the dialyzer 2 flows through the dialysate-discharge tube L2 and is discharged to the outside. The storage bag B1 is hooked on any of hooks F provided on the dialysate apparatus and is weighed by a gravimeter 3 on a real-time basis. Hence, the dialysate is supplied to and discharged from the dialyzer 2 at a preset flow rate.

In the present embodiment, the squeezable flexible tube D3 is connected to the substitution-fluid-introduction tube L3 branching off from the dialysate-introduction tube L1 and is attached to the peristaltic pump P3. When the peristaltic pumps P2 and P3 are activated, the dialysate in the storage bag B1 is supplied to the air-trap chamber 5 connected to the venous blood circuit 1b, whereby a substitution fluid layer can be formed therein. The peristaltic pump P3 corresponds to "a substitution-fluid-infusion device that is capable of infusing a substitution fluid" according to the present invention. The air-trap chamber 5 may be connected to the arterial blood circuit 1a, and the dialysate may be supplied to the air-trap chamber 5 with the distal end of the substitution-fluid-introduction tube L3 being connected thereto.

As illustrated in FIGS. 2 and 3, the air-trap chamber 5 is attached to the case C, and the substitution-fluid-introduction tube L3 and the blood circuit 1 (the venous blood circuit 1b) are connected to the air-trap chamber 5. The air-trap chamber 5 is a chamber having a storing space connected to the blood circuit 1 (the venous blood circuit 1b) through which blood flows. In the storing space, an air layer, a substitution fluid layer, and a blood layer can be formed in that order from the top. Air contained in the blood flowing through the blood circuit 1 is collected in the air layer and is removed from the blood. As illustrated in FIG. 4, the air-trap chamber 5 has a blood inlet 5a, a blood outlet 5b, a substitution fluid inlet 5c, and an air inlet/outlet 5d.

The blood inlet 5a and the blood outlet 5b are provided at respective points of connection to the venous blood circuit 1b and allow the blood to flow into and out of the air-trap chamber 5, respectively. The substitution fluid inlet 5c is provided at a point of connection to the substitution-fluid-introduction tube L3 and allows the substitution fluid to flow into the air-trap chamber 5. An airflow tube L4 that allows air to flow therethrough is connected to a top part (the air layer) of the air-trap chamber 5. The air inlet/outlet 5d is provided at a point of connection to the airflow tube L4.

The air-volume-adjusting device 8 that can infuse and discharge air into and from the air layer is connected to the airflow tube L4. For example, the airflow tube L4 forms a flow route that is made of a flexible tube or the like whose distal end is open to the atmosphere. The air-volume-adjusting device 8, which is a peristaltic pump, is provided at a halfway point of the airflow tube L4. The air-volume-adjusting device 8 includes a squeezing unit that is rotatable in the normal direction and in the reverse direction. The squeezing unit squeezes the airflow tube L4 in the lengthwise direction of the airflow tube L4, whereby air can arbitrarily be infused into and discharged from the top part of the air-trap chamber 5.

When the air-volume-adjusting device 8 is rotated in the normal direction (the direction of rotation with which air is infused into the air-trap chamber 5), air is taken from the distal end of the airflow tube L4. Since the taken air is infused into the air-trap chamber 5, the interface of the air layer is lowered. When the air-volume-adjusting device 8 is rotated in the reverse direction (the direction of rotation with which air is discharged from the air-trap chamber 5), air is discharged from the distal end of the airflow tube L4. Since the air is discharged from the air-trap chamber 5, the interface of the air layer can be raised. As described above, the air-volume-adjusting device 8 according to the present embodiment includes the squeezing unit capable of rotating in the normal direction and in the reverse direction. However, the present invention is not limited to such an embodiment. Any other embodiment may be implemented as long as air can be infused into and discharged from the air layer formed in the air-trap chamber 5.

The air-trap chamber 5 may be replaced with, for example, an air-trap chamber 5' illustrated in FIG. 5. The air-trap chamber 5' has a blood inlet 5'a and a substitution fluid inlet 5'c that are provided inside the air-trap chamber 5. The substitution fluid inlet 5'c is provided at a higher level than the blood inlet 5'a. The blood outlet 5'b and the air inlet/outlet 5'd are the same as those of the air-trap chamber 5. In the air-trap chamber 5' also, an air layer, a substitution fluid layer, and a blood layer can be formed in the storing space thereof in that order from the top.

The blood-interface-detecting device 6 is capable of detecting the interface between the blood layer and the substitution fluid layer that are formed in the air-trap chamber 5. The blood-interface-detecting device 6 according to the present embodiment is a photosensor that is capable of detecting the interface between the blood layer and the substitution fluid layer in a non-contact manner from an outer side face of the air-trap chamber 5. Specifically, the blood-interface-detecting device 6 includes a light-emitting element and a light-receiving element that are provided as a pair and are arranged across the air-trap chamber 5 from each other in the horizontal direction (the diametrical direction of the air-trap chamber 5).

For example, the light-emitting element is an LED (a near-infrared LED) capable of emitting near infrared rays, and the light-receiving element is a photodiode. When the light-emitting element emits light, the light travels through the air-trap chamber 5 in the diametrical direction and is received by the light-receiving element (a configuration of a so-called transmission sensor). Since the amount of light transmission is different between the substitution fluid and the blood, the interface between the blood layer and the substitution fluid layer is detectable on the basis of the voltage generated at the light reception by the light-receiving element. While the present embodiment employs the blood-interface-detecting device 6 as a transmission sensor, the interface between the blood layer and the substitution fluid layer may be detected on the basis of the light received after being reflected in the air-trap chamber 5 (a configuration of a so-called reflection sensor). Alternatively, the blood-interface-detecting device 6 may be an ultrasonic sensor, so that the interface between the blood layer and the substitution fluid layer can be detected on the basis of the ultrasonic wave transmitted through or reflected in the air-trap chamber 5.

In the present embodiment, the interface between the blood layer and the substitution fluid layer is detectable on the basis of the voltage generated at the light reception by the light-receiving element in consideration of a predetermined duty ratio. Hence, even if the pulsation generated by the driving of the blood pump P1 causes the interface between the blood layer and the substitution fluid layer to be periodically raised and lowered, the interface can be detected accurately while the occurrence of misdetection is prevented. When bubbles (air) come up from the blood in the blood layer toward the air layer, a slight amount of blood may be caught by the bubbles and reach the substitution fluid layer, leading to a misdetection of the interface. However, such a misdetection can be suppressed as long as the detection of the interface between the blood layer and the substitution fluid layer is performed at the predetermined duty ratio.

The air-interface-detecting device 7 is capable of detecting the interface between the substitution fluid layer and the air layer that are formed in the air-trap chamber 5. The air-interface-detecting device 7 according to the present embodiment is an ultrasonic sensor capable of detecting the interface between the substitution fluid layer and the air layer in a non-contact manner from an outer side face of the air-trap chamber 5. Specifically, the air-interface-detecting device 7 includes an ultrasonic vibration element and an ultrasonic receiving element that are provided as a pair and are arranged across the air-trap chamber 5 from each other in the horizontal direction (the diametrical direction of the air-trap chamber 5).

The ultrasonic vibration element is capable of emitting ultrasonic waves toward the air-trap chamber 5, and the ultrasonic receiving element is capable of receiving the waves as vibration. The ultrasonic receiving element generates a voltage that varies with the vibration received. On the basis of the voltage, the interface between the substitution fluid layer and the air layer that are formed in the air-trap chamber 5 is detectable. Specifically, since air damps ultrasonic waves at a higher rate than the substitution fluid, the interface between the substitution fluid layer and the air layer can be detected on the basis of the voltage generated by the ultrasonic receiving element.

As illustrated in FIG. 6, the air-interface-detecting device 7 may include an upper position sensor 7a provided on the upper side and including an ultrasonic vibration element and an ultrasonic receiving element that are provided as a pair, and a lower position sensor 7b provided on the lower side and including an ultrasonic vibration element and an ultrasonic receiving element that are provided as a pair. In such a case, the upper position sensor 7a is positioned at the highest possible level of the air layer, while the lower position sensor 7b is positioned at the lowest possible level of the air layer.

In the present embodiment, the interface between the substitution fluid layer and the air layer is detectable on the basis of the voltage generated at the detection by the ultrasonic receiving element in consideration of a predetermined duty ratio. Hence, even if the pulsation generated by the driving of the blood pump P1 causes the interface between the substitution fluid layer and the air layer to be periodically raised and lowered, the interface can be detected accurately while the occurrence of misdetection is prevented. The air-interface-detecting device 7 may be a photosensor that detects the interface between the substitution fluid layer and the air layer by detecting the light transmitted or reflected.

The blood-interface-detecting device 6 and the air-interface-detecting device 7 are each not limited to a photosensor or an ultrasonic sensor described above and may each be configured to detect the interface between the blood layer and the substitution fluid layer or the interface between the substitution fluid layer and the air layer by taking an image of an outer side face of the air-trap chamber 5 and analyzing the image. In such a case also, it is preferable to perform the detection of the interface between the blood layer and the substitution fluid layer or the interface between the substitution fluid layer and the air layer on the basis of the image analyzed at a predetermined duty ratio.

In the present embodiment, the blood-interface-detecting device 6, the air-interface-detecting device 7, the air-volume-adjusting device 8, the blood pump P1, and the peristaltic pump P3 (the substitution-fluid-infusion device) are each electrically connected to the control unit E. The control unit E is a microcomputer or the like provided in the dialysis-apparatus body A. The control unit E is capable of detecting the lack of substitution fluid in the air-trap chamber 5 on the basis of the interface between the blood layer and the substitution fluid layer that is detected by the blood-interface-detecting device 6. The control unit E is also capable of issuing a predetermined notification if any lack of substitution fluid in the air-trap chamber 5 is detected. The predetermined notification is made by any of the following ways, for example: an indication representing the lack of substitution fluid is displayed on the monitor M of the dialysis-apparatus body A, a warning lamp is turned on or is made to blink, an alarm sound is generated from a speaker, and so forth.

If any lack of substitution fluid in the air-trap chamber 5 is detected, the control unit E controls the blood pump P1 or the peristaltic pump P3 (the substitution-fluid-infusion device) to reduce the volume of the blood layer or to increase the volume of the substitution fluid layer in the air-trap chamber 5. That is, if the volume of the blood layer in the air-trap chamber 5 is reduced by stopping the blood pump P1 or by reducing the flow rate of the blood, the volume of the substitution fluid layer can be made relatively large, whereby the lack of substitution fluid can be solved. Alternatively, if the peristaltic pump P3 (the substitution-fluid-infusion device) is activated or if the flow rate of the substitution fluid is increased, the volume of the substitution fluid layer is directly increased, whereby the lack of substitution fluid can be solved.

In the blood purification apparatus according to the above embodiment, the peristaltic pump P3 (the substitution-fluid-infusion device) capable of infusing the substitution fluid is connected to the air-trap chamber 5, and a substitution fluid layer can therefore be formed on the blood layer. Furthermore, the air-trap chamber 5 is provided with the blood-interface-detecting device 6 capable of detecting the interface between the blood layer and the substitution fluid layer that are formed in the air-trap chamber 5, so that the lack of substitution fluid in the air-trap chamber 5 can be detected on the basis of the interface between the blood layer and the substitution fluid layer that is detected by the blood-interface-detecting device 6. Hence, the lack of substitution fluid in the air-trap chamber 5 can be recognized quickly and correctly.

Furthermore, if any lack of substitution fluid in the air-trap chamber 5 is detected, a predetermined notification is issued. Therefore, the lack of substitution fluid in the air-trap chamber 5 can be recognized more quickly and correctly. Furthermore, if any lack of substitution fluid in the air-trap chamber 5 is detected, the blood pump P1 or the peristaltic pump P3 (the substitution-fluid-infusion device) is controlled to reduce the volume of the blood layer or to increase the volume of the substitution fluid layer. Therefore, the lack of substitution fluid in the air-trap chamber 5 can be solved automatically.

Furthermore, the blood-interface-detecting device 6 is capable of detecting the interface between the blood layer and the substitution fluid layer in a non-contact manner from an outer side face of the air-trap chamber 5 and at a predetermined duty ratio. Therefore, the misdetection of the lack of substitution fluid that is caused by, for example, the pulsation generated by the driving of the blood pump P1 can be suppressed, and the accuracy can further be increased. In addition, the air-trap chamber 5 in which an air layer can be formed on the substitution fluid layer is connected to the air-volume-adjusting device 8 capable of infusing and discharging air into and from the air layer, and the air-trap chamber 5 is provided with the air-interface-detecting device 7 capable of detecting the interface between the substitution fluid layer and the air layer that are formed in the air-trap chamber 5. Therefore, the interface of the air layer in the air-trap chamber 5 can be set to an appropriate level by using the air-volume-adjusting device 8. Accordingly, the substitution fluid layer can have an appropriate volume.

While the present embodiment has been described above, the present invention is not limited thereto. For example, as illustrated in FIG. 7, with the activation of the peristaltic pump P3 (the substitution-fluid-infusion device), the substitution fluid, such as a physiological saline solution, stored in a storage bag B2 may be supplied to the air-trap chamber 5 connected to the venous blood circuit 1b so that a substitution fluid layer can be formed, and the blood-interface-detecting device 6 may detect the interface between the blood layer and the substitution fluid layer that are formed in the air-trap chamber 5.

Furthermore, it is only necessary that the lack of substitution fluid in the air-trap chamber 5 is detectable on the basis of the interface between the blood layer and the substitution fluid layer that is detected by the blood-interface-detecting device 6. Hence, if any lack of substitution fluid in the air-trap chamber 5 is detected, only a predetermined notification may be issued without activating the blood pump P1 and the peristaltic pump P3 (the substitution-fluid-infusion device), or only the blood pump P1 or the peristaltic pump P3 (the substitution-fluid-infusion device) may be activated without issuing the predetermined notification. Alternatively, even if any lack of substitution fluid in the air-trap chamber 5 is detected, neither the issuing of a predetermined notification nor the activation of the blood pump P1 or the peristaltic pump P3 (the substitution-fluid-infusion device) may be performed as long as any other solution for the lack of substitution fluid can be made.

Furthermore, the blood-interface-detecting device 6 and the air-interface-detecting device 7 are each not limited to a photosensor or an ultrasonic sensor and may be any other device as long as it is capable of detecting the interface in a non-contact manner by using electromagnetic waves. Furthermore, the interface may be detected without being based on a predetermined duty ratio. While the present embodiment is applied to a dialysis apparatus intended for hemodialysis treatment, the present invention is also applicable to any other apparatuses that are capable of purifying the blood of the patient while extracorporeally circulating the blood (such as a blood purification apparatus, a plasma absorption apparatus, and the like intended for blood-filtering dialysis treatment, a blood filtering method, and AFBF).

The present invention is applicable to any blood purification apparatuses such as those having other functions, as long as the substitution-fluid-infusion device that is capable of infusing the substitution fluid is connected to the air-trap chamber; a substitution fluid layer can be formed on the blood layer in the air-trap chamber; the air-trap chamber is provided with the blood-interface-detecting device that is capable of detecting the interface between the blood layer and the substitution fluid layer that are formed therein; and the lack of substitution fluid in the air-trap chamber is detectable on the basis of the interface between the blood layer and the substitution fluid layer that is detected by the blood-interface-detecting device.

REFERENCE SIGNS LIST 1 blood circuit
2 dialyzer (blood purifier)
3 gravimeter
5 air-trap chamber
6 blood-interface-detecting device
7 air-interface-detecting device
8 air-volume-adjusting device
P1 blood pump
P3 peristaltic pump (substitution-fluid-infusion device)

The invention claimed is:
1. A blood purification apparatus comprising:
 a blood circuit including an arterial blood circuit and a venous blood circuit and through which blood of a patient is allowed to extracorporeally circulate from a distal end of the arterial blood circuit to a distal end of the venous blood circuit;
 a blood purification device interposed between the arterial blood circuit and the venous blood circuit of the blood circuit that is capable of purifying the blood flowing through the blood circuit;
 a blood pump provided to the arterial blood circuit that delivers the blood in the blood circuit;
 an air-trap chamber connected to the blood circuit that collects air in the blood flowing through the blood circuit, the air trap chamber comprising:
 a substitution-fluid inlet; and
 an air inlet and an air outlet for an air layer located within the air-trap chamber;
 a substitution fluid layer that is provided on a blood layer and under the air layer in the air-trap chamber so that the air layer is free of contact with the blood layer;
 a substitution-fluid-infusion device that infuses a substitution fluid into the air-trap chamber by the substitution-fluid inlet so that the substitution fluid is distributed in the substitution fluid layer;

an air-volume-adjusting device is connected to the air inlet and the air outlet of the air-trap chamber that is capable of infusing and discharging air into and from the air layer;
a blood-interface-detecting device that detects an interface between the blood layer and the substitution fluid layer that are formed in the air-trap chamber; and
wherein a lack of the substitution fluid in the air-trap chamber is detectable on a basis of the interface between the blood layer and the substitution fluid layer that is detected by the blood-interface-detecting device; and if the lack of the substitution fluid in the air-trap chamber is detected, the blood pump or the substitution-fluid-infusion device is controlled to reduce a volume of the blood layer or to increase a volume of the substitution fluid layer in order to solve the lack of the substitution fluid.

2. The blood purification apparatus according to claim 1, wherein the blood purification apparatus is capable of issuing a predetermined notification if the lack of the substitution fluid in the air-trap chamber is detected.

3. The blood purification apparatus according to claim 1, wherein the blood-interface-detecting device is capable of detecting the interface between the blood layer and the substitution fluid layer in a non-contact manner from an outer side face of the air-trap chamber and at a predetermined duty ratio.

4. The blood purification apparatus according to claim 1, wherein the air layer is formable on the substitution fluid layer in the air-trap chamber; and the air-trap chamber is provided with an air-interface-detecting device that is capable of detecting an interface between the substitution fluid layer and the air layer that are formed in the air-trap chamber.

5. The blood purification apparatus according to claim 2, wherein the blood-interface-detecting device is capable of detecting the interface between the blood layer and the substitution fluid layer in a non-contact manner from an outer side face of the air-trap chamber and at a predetermined duty ratio.

6. The blood purification apparatus according to claim 2, wherein the air layer is formable on the substitution fluid layer in the air-trap chamber; and the air-trap chamber is provided with an air-interface-detecting device that is capable of detecting an interface between the substitution fluid layer and the air layer that are formed in the air-trap chamber.

7. The blood purification apparatus according to claim 3, wherein the air layer is formable on the substitution fluid layer in the air-trap chamber; and the air-trap chamber is provided with an air-interface-detecting device that is capable of detecting an interface between the substitution fluid layer and the air layer that are formed in the air-trap chamber.

8. The blood purification device according to claim 4, wherein the air-interface-detecting device includes a transmitting element and a receiving element positioned across the air-trap chamber from each other in a diametrical direction of the air-trap chamber and in communication with each other.

9. The blood purification device according to claim 8, wherein the transmitting element is a light-emitting element and the receiving element is a light-receiving element configured to send a signal across the diametrical direction of the air-trap chamber between the transmitting element and the receiving element.

10. The blood purification device according to claim 8, wherein the transmitting element is an ultrasonic vibration element and the receiving element is an ultrasonic receiving element configured to send a signal across the diametrical direction of the air-trap chamber between the transmitting element and the receiving element.

11. The blood purification device according to claim 8, wherein the transmitting element of the air-interface-detecting device is a pair of transmitting elements and the receiving element of the air-interface-detecting device is a pair of receiving elements.

12. The blood purification device according to claim 1, wherein the air-trap chamber is connected to an airflow tube and the air inlet is provided at a point of connection to the airflow tube.

13. A blood purification apparatus comprising:
a blood circuit including an arterial blood circuit and a venous blood circuit and through which blood of a patient is allowed to extracorporeally circulate from a distal end of the arterial blood circuit to a distal end of the venous blood circuit;
a blood purification device interposed between the arterial blood circuit and the venous blood circuit of the blood circuit that is capable of purifying the blood flowing through the blood circuit;
a blood pump provided to the arterial blood circuit that delivers the blood in the blood circuit;
an air-trap chamber connected to the blood circuit and that is capable of collecting air in the blood flowing through the blood circuit, the air trap chamber comprising:
a substitution-fluid inlet; and
an air inlet and an air outlet in communication with an air layer located within the air-trap chamber; and
a monitor,
a substitution-fluid-infusion device that infuses a substitution fluid into the air-trap chamber by the substitution-fluid inlet so that the substitution fluid is distributed in the substitution fluid layer;
a substitution fluid layer is provided on a blood layer and under the air layer in the air-trap chamber, so that the air layer is free of contact with the blood layer;
an air-volume-adjusting device is connected to the air inlet and the air outlet of the air-trap
chamber that is capable of infusing and discharging air into and from the air layer:
a blood-interface-detecting device that detects an interface between the blood layer and the substitution fluid layer that are formed in the air-trap chamber; and
wherein a lack of the substitution fluid in the air-trap chamber is detectable on a basis of the interface between the blood layer and the substitution fluid layer that is detected by the blood-interface-detecting device; and if the lack of the substitution fluid in the air-trap chamber is detected, an indication representing the lack of the substitution fluid is displayed on the monitor in order to solve the lack of the substitution fluid.

14. The blood purification apparatus according to claim 13, wherein, if the lack of the substitution fluid in the air-trap chamber is detected, the blood pump or the substitution-fluid-infusion device is controlled to reduce a volume of the blood layer or to increase a volume of the substitution fluid layer.

15. The blood purification apparatus according to claim 14, wherein the blood-interface-detecting device is capable of detecting the interface between the blood layer and the substitution fluid layer in a non-contact manner from an outer side face of the air-trap chamber and at a predetermined duty ratio.

16. The blood purification apparatus according to claim 14, wherein the air layer is formable on the substitution fluid layer in the air-trap chamber; and the air-trap chamber is provided with an air-interface-detecting device that is capable of detecting an interface between the substitution fluid layer and the air layer that are formed in the air-trap chamber.

17. The blood purification device according to claim 16, wherein the air-interface-detecting device includes a transmitting element and a receiving element positioned across the air-trap chamber from each other in a diametrical direction of the air-trap chamber and in communication with each other; and wherein the transmitting element of the air-interface-detecting device is a pair of transmitting elements and the receiving element of the air-interface-detecting device is a pair of receiving elements.

18. The blood purification device according to claim 17, wherein the transmitting element is an ultrasonic vibration element and the receiving element is an ultrasonic receiving element configured to send a signal across the diametrical direction of the air-trap chamber between the transmitting element and the receiving element.

19. The blood purification device according to claim 17, wherein the transmitting element is a light-emitting element and the receiving element is a light-receiving element configured to send a signal across the diametrical direction of the air-trap chamber between the transmitting element and the receiving element.

20. The blood purification device according to claim 13, wherein the air-trap chamber is connected to an airflow tube and the air inlet is provided at a point of connection to the airflow tube.

* * * * *